United States Patent [19]

Pigerol et al.

[11] 4,223,041
[45] Sep. 16, 1980

[54] UREA DERIVATIVES TO TREAT ANXIETY AND AGGRESSIVITY

[75] Inventors: Charles Pigerol, Saint-Ouen; Pierre Eymard, Fontaine; Jean-Claude Vernieres, Domene; Madeleine Combet epse Broll, St. Egreve; Jean-Yves Lacolle, Domene, all of France

[73] Assignee: Labaz, Paris, France

[21] Appl. No.: 844,618

[22] Filed: Oct. 25, 1977

[30] Foreign Application Priority Data

Nov. 4, 1976 [FR] France .................. 76 33213

[51] Int. Cl.² ............................................. A61K 31/17
[52] U.S. Cl. .............................. 424/322; 260/553 R; 260/555 R
[58] Field of Search ............... 424/322; 260/555 R, 260/553 R

[56] References Cited

U.S. PATENT DOCUMENTS

| | | | |
|---|---|---|---|
| 2,999,110 | 9/1961 | Lott | 424/254 |
| 3,110,728 | 11/1963 | Takamatsu et al. | 260/553 E |
| 4,026,925 | 5/1977 | Pigerol et al. | 424/325 |

OTHER PUBLICATIONS

Chem. Abst., 7th Coll. Formulas $C_{11}H_{13}$—$G_6H_{23}$, p. 1813F.
Chem. Abst., 80-36814j (1974).
Arch. Int. Pharmacodyn, 219 pp. 103–115 (1976).
Arch. Int. Pharmacodyn, 208 pp. 204–212 (1974).

*Primary Examiner*—Stanley J. Friedman
*Attorney, Agent, or Firm*—Mason, Kolehmainen, Rathburn & Wyss

[57] ABSTRACT

Urea derivatives of the formula:

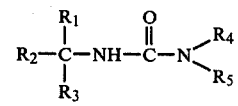

wherein $R_1$, $R_2$ and $R_3$, which are the same or different, each represent a straight- or branched-chain alkyl, alkenyl or alkynyl radical having from 1 to 5 carbon atoms, $R_4$ and $R_5$, which are the same or different, each represent a hydrogen atom or a straight- or branched-chain alkyl, alkenyl or alkynyl radical having from 1 to 5 carbon atoms, $R_1$, $R_2$ and $R_3$ being such that:

(a) only one of these radicals can represent an alkenyl or alkynyl group having an unsaturated bond in the $\alpha,\beta$-position with respect to the methylurea radical, in this case, each of the other two substituents represents an alkyl radical, (b) the sum of their carbon atoms is never inferior to 4.

They are useful as anxiolytic and antiagressive agents.

3 Claims, No Drawings

UREA DERIVATIVES TO TREAT ANXIETY AND AGGRESSIVITY

This invention relates to urea derivatives having pharmacological activity and to pharmaceutical and veterinary compositions containing them.

The invention is also concerned with a process for preparing the said urea derivatives as well as a process for preparing the compositions containing the same.

The pharmacologically active compounds with which the invention is concerned can be represented by the general formula:

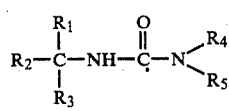

wherein $R_1$, $R_2$ and $R_3$, which are the same or different, each represent a straight- or branched-chain alkyl, alkenyl or alkynyl radical having from 1 to 5 carbon atoms, $R_4$ and $R_5$ which are the same or different, each represent a hydrogen atom or a straight- or branched-chain alkyl, alkenyl or alkynyl radical having from 1 to 5 carbon atoms, $R_1$, $R_2$ and $R_3$ being such that:

(a) only one of these radicals can represent an alkenyl or alkynyl group having an unsaturated bond in the α, β-position with respect to the methylurea radical, in this case, each of the other two substituents represents an alkyl radical.

(b) the sum of their carbon atoms is never inferior to 4.

Some of the compounds of formula I possess an asymetric carbon.

With respect to such compounds, the invention relates to the racemic mixtures and to the corresponding optical isomers.

As will be described in greater detail further on, it has been found that the urea derivatives of the invention are endowed with marked pharmacological properties capable of rendering them useful in human and veterinary therapy and, in particular, in the treatment of pathological states of anxiety and aggressivity.

Another object of the present invention is consequently a pharmaceutical or veterinary composition for use in the treatment of pathological states of anxiety and aggressivity, the said composition comprising, as essential active ingredient, at least one urea derivative of formula I, in association with a pharmaceutical carrier or excipient therefor.

A further object of the present invention is to provide a process for preparing pharmaceutical and veterinary compositions for treating pathological states of anxiety and aggressivity whereby at least one urea derivative, as defined in formula I, is associated with an appropriate pharmaceutical carrier or excipient.

Yet another object of the present invention is to provide a method of treating pathological states of anxiety and aggressivity in a host in need of such treatment, such method comprising the administration to said host of an effective dose of at least one urea derivative of formula I.

In the case of a human being weighing 60 kg, the daily dosage will preferably be between 400 and 1200 mg of active principle.

Amongst the compounds of formula I, a certain number are known products having been specifically cited in previous patents or publications.

For example, 1-(1,1-di-n-butyl-n-pentyl)-urea, 1-(1,1-dimethyl-n-butyl)-urea, 1-(1,1-dimethyl-n-propyl)-urea, 1-(1-methyl-1-ethyl-n-propyl)-urea, 1-(1,1-dimethyl-n-pentyl)-urea, 1-(1,1,3,3-tetramethyl-n-butyl)-urea, 1-(1,1,3,3-tetramethyl-n-pentyl)-urea and 1-(1,1-dimethylethyl)-urea, are all described in U.S. Pat. No. 3,847,981.

However, no pharmacological activity of any sort is cited in this patent with respect to such derivatives.

In Chemical Abstracts 80, 74, 36814 j some derivatives of 1-(2-propynyl)-urea are cited namely 1-(1,1-dimethyl-2-propynyl)-urea, 1-(1-methyl-1-ethyl-2-propynyl)-urea and 1-(1-methyl-1-n-propyl-2-propynyl)-urea without any mention of pharmacologial properties regarding them.

Similarly, U.S. Pat. No. 3,852,473 describes 1-(1,1-dimethyl-ethyl)-urea, 1-(1,1-dimethyl-propyl)-urea and 1-(1-methyl-1-ethyl-propyl)-urea.

This aforesaid U.S. Patent also mentions generically all of the other derivatives of formula I hereabove and states that the said derivatives can constitute agents capable of inducing polyphagia and accelerating growth in animals, for example, in cattle.

As these properties have been verified only with respect to the three above-mentioned derivatives, it cannot be reasonably concluded that all the derivatives covered by the U.S. Patent in question possess the said properties.

Furthermore, certain derivatives of formula I can be considered as novel products because they are neither specifically cited nor described in the state of the art.

Therefore, another object of the invention is to provide, as novel compounds, the urea derivatives of general formula I wherein $R_1$ and $R_3$, which are the same, each represent ethyl or n-propyl, $R_2$ represents ethyl, n-propyl, isopropyl, 2-methyl-propyl, allyl, ethynyl, 1-propynyl or 1-butynyl, $R_4$ represents hydrogen, methyl, allyl or propargyl and $R_5$ represents hydrogen or methyl.

A class or preferred compounds of formula I are those wherein $R_1$ and $R_3$, which are identical, represent ethyl or n-propyl, $R_2$ represents ethyl, n-propyl, allyl, ethynyl, 1-propynyl or 1-butynyl and $R_4$ and $R_5$ each represent hydrogen.

Another class or preferred compounds of the invention can be represented by the general formula:

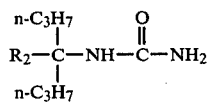

wherein $R_2$ represents n-propyl, allyl, 1-propynyl or 1-butynyl.

The compounds of formula I hereabove can be prepared by reacting, in an appropriate solvent such as, for example, water, ethyl ether, heptane, benzene, toluene, an isocyanate of the general formula:

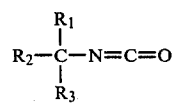

wherein $R_1$, $R_2$ and $R_3$ have the same meaning as in formula I, with a compound of the general formula:

$$R_4\text{—NH—}R_5 \qquad \text{III}$$

in which $R_4$ and $R_5$ have the same meaning as in formula I, which provides the required derivative of formula I.

In accordance with a preferred procedure, the isocyanate of formula II will be added to the compound of formula III dissolved in the chosen solvent.

With regard to the reaction temperature, this will lie between room temperature and the boiling temperature of the solvent employed.

In the case of the compound of formula III wherein $R_4$ and $R_5$ each represent hydrogen, namely ammonia, this reagent can be utilized in the form of an aqueous solution or dissolved in an organic solvent such as dioxan.

In accordance with another procedure, the compounds of formula I wherein $R_4$ and $R_5$ each represent hydrogen can be obtained by heating a methylamine derivative of the general formula:

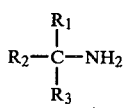

wherein $R_1$, $R_2$ and $R_3$ have the same meaning as in formula I, with nitrourea, which provides the desired compound of the invention.

Advantageously, the reaction will be carried out in water by heating the reagents together at a temperature between 30° C. and 70° C., preferably about 50° C.

This last-cited method will be used, particularly, for preparing urea derivatives of the invention having an unsaturated bond in the $\alpha$, $\beta$-position with respect to the trisubstituted methylurea radical.

Similarly, the compounds of formula I wherein $R_4$ represents a straight- or branched-chain alkyl, alkenyl or alkynyl radical having from 1 to 5 carbon atoms and $R_5$ represents hydrogen can also be prepared by reacting at room temperature or by heating, in a appropriate solvent such as for example ethyl ether, a methylamine derivative of formula IV hereabove with an isocyanate of the general formula:

$$R_4\text{—N=C=O} \qquad \text{V}$$

wherein $R_4$ has the same meaning as given above, which provides the desired compound of the invention.

The temperature of the reaction will vary according to the reagents involved and will be preferably between room temperature and 110° C.

In accordance with a preferred procedure, the amine of formula IV will be added to the isocyanate of formula V dissolved in the chosen solvent.

Some of the compounds of formulae II and IV have been specifically cited in U.S. Pat. No. 4,026,925. The other compounds of formulae II and IV can be prepared by the methods described in the said U.S. Patent.

Urea derivatives are already known which possess pharmacological properties in respect of the central nervous system and more particularly tranquillizing, anxiolytic, muscle relaxant, sedative, hypnotic and anticonvulsant properties.

Certain of these derivatives are already commercialized such as phenylacetylurea, bromodiethylacetylurea and α-bromoisovalerylurea while others have been described in previous pulbications or patents, for example in U.S. Pat. Nos. 2,999,100 and 3,110,728, British Pat. No. 1,056,833, French Pat. No. 5341 M as in Pat. No. 21,573 of the German Democratic Republic.

The urea derivatives cited as tranquillizing or anxiolytic agents in the aforesaid patents are characterized by the presence in their molecule of heteroatoms additional to those forming the urea radical. In this connection, halogen and oxygen atoms more particularly in the form of carbonyl or hydroxyl radicals can be cited.

Furthermore, tert-butyl-urea is described in Arch. Int. Pharmacodyn 219, 104—115 (1976) as an agent having anticonvulsant, hypnotic and sedative properties and as a potentiator of the hypnotic effects of the barbiturates. Similarly, n-butyl-urea is described in Arch. Int. Pharmacodyn 208, 204–212 (1974) as possessing properties similar to those cited hereabove with respect to tert-butyl-urea.

However, no allusion is made in these publications to the possibility that n-butyl- or tert-butyl-urea may possess anxiolytic or anti-aggressive properties.

Five derivatives of urea are described in Chimie Therapeutique No. 4, pp. 412 to 418, one of them being 1-(1-methyl-2-propyl-pentyl)-3-cyclohexyl-urea.

The reference in question states that several pharmacological trials were carried out with the five compounds described therein.

No tranquillizing activity of the anxiolytic or antiaggressive type is mentioned regarding these compounds.

It has now been surprisingly discovered that the urea derivatives of formula I having a chemical structure similar to that of 1-(1-methyl-2-propyl-pentyl)-3-cyclohexyl-urea, tert-butyl-urea and n-butyl-urea, namely urea derivatives characterized by the absence of heteroatoms but by the presence of only hydrocarbon radicals of the aliphatic type present valuable anxiolytic and antiaggressive properties.

This observation is all the more unexpected since trisubstituted derivatives of methyl-urea similar to those of formula I i.e. having in the 3-position a radical generally present in the urea derivatives which are active as tranquillizers or anxiolytics were found to be inactive or practically devoid of any anxiolytic or antiaggressive activity. As examples of such compounds, 1-(1,1-di-n-propyl-n-butyl)-3-benzoyl- or 3-acetyl-urea can be cited.

In addition, the anxiolytic properties of the compounds of the invention have been found to exert their effect at doses inferior to those influencing behaviour and motoricity. This observation was certainly not predictable from the state of the art and particularly from French Medicament Pat. No. 5341 M.

The derivatives covered by this French Medicament Patent are, in fact, presented as possessing anxiolytic properties at sedative doses.

The possibility thus offered by the compounds of the invention of separating anxiolytic effects from sedative effects constitutes a very appreciable advantage over the compounds covered by the French Medicament Patent in question and over certain commercially available products such as diazepam and meprobamate.

It is, in fact, known that a certain degree of somnolence and loss of power to concentrate are amongst the most frequent disadvantages presented by such tranquilizers.

For this reason, diazepam and meprobamate must be used with caution in ambulatory therapy by patients having a professional activity requiring close attention and by drivers of vehicles.

As against this, the compounds of the invention will constitute a valuable advance over present therapy since they do not exert any sedative or hypnotic activity at doses useful against anxiety. Thus, the compounds of the invention will enable patients to avoid a certain number of contra-indications which hamper treatment with the presently available anxiolytics since they do not affect the power to concentrate.

Another characteristic of the compounds of the invention is their very low toxicity.

This advantage is particularly important in psychiatry since suicide attempts by overdosage are very frequent in that field.

Finally, the compounds of the invention, when given at tranquillizing doses, will not exert any undesirable side-effects due to central or peripheral anticholinergic activity, such as dryness of the mouth, difficulty in optical accommodation, sweating and tachycardia.

The compounds of the invention have, in fact, been found to be devoid of such disadvantages.

From this point of view, the compounds of the invention will constitute valuable additions to the therapeutic arsenal at the disposal of the doctor and, if necessary, will provide useful replacement medication for a drug which has become ineffective for any reason such as, for example, a change in the state of the patient or habituation.

The compound of the invention which has shown the most outstanding anxiolytic and antiaggressive properties is 1-(1,1-di-n-propyl-n-butyl)-urea or tri-n-propylmethylurea.

Additional pharmacological tests carried out with the preferred compound of the invention have shown that a non-sedative dose of this compound potentiates the hypnotic effect of the barbiturates as well as the sedative effect of tranquillizers such as meprobamate and diazepam. On the other hand, the preferred compound of the invention only produces slight potentiation of the effects of ethanol.

Furthermore, the preferred compound of the invention has no appreciable action on the cardiovascular or respiratory system.

It has, in fact, been demonstrated that, at intreperitoneal doses of 100 and 200 mg/kg, the preferred compound of the invention does not modify systemic arterial blood pressure, cardiac frequency and respiratory frequency in the anaesthetized rat.

Similarly, at a dose of 100 mg/kg by intraperitoneal route, the preferred compound of the invention has no influence on acetylcholine-induced hypotension and bradycardia in the rat. The intraperitoneal injection of a double does, namely 200 mg/kg, does not modify either the α-adrenergic or the β-adrenergic effects provoked by epinephrine.

Since the preferred compound of the invention is devoid of these undesirable side-effects, it will not provoke either cardiac disturbances or disturbances of arterial pressure.

Pharmacological trials have been carried out in order to determine the toxicity of the compounds of the invention as well as the precence of the different properties which will render these compounds useful as tranquillizers.

As examples, the results obtained with the following compounds of formula I are given further on:
1-(1,1-Di-n-propyl-n-butyl)-urea (Compound A)
1-(1,1-Di-n-propyl-2-pentynyl)-urea (Compound B)
1-(1,1-Diethyl-2-propynyl)-urea (Compound C)
1-(1,1-Di-n-propyl-2-butynyl)-urea (Compound D)
1-(1,1-Di-n-propyl-3-butenyl)-urea (Compound E)
1-(1,1-Diethyl-n-propyl)-urea (Compound F)
1-(1-Methyl-1-ethyl-pentyl)-urea (Compound G)
1-(1-n-Propyl-1-isopropyl-n-butyl)-urea (Compound H)
1-(1,1-Di-n-propyl-n-butyl)-3,3-dimethyl-urea (Compound I)
1-(1,1-Di-n-butyl-n-pentyl)-urea (Compound J)
1-(1,1-Di-n-propyl-n-butyl)-3-methyl-urea (Compound K)
1-(1,1-Di-n-propyl-3-butenyl)-3-methyl-urea (Compound L)
1-(1,1-Di-n-propyl-n-butyl)-3-(2-propynyl)-urea (Compound M)
1-(1,1-Di-n-propyl-n-butyl)-3-(2-propenyl)-urea (Compound N)
1-(1,1-Di-n-propyl-3-methyl-n-butyl)-urea (Compound P)

I. Action on behaviour

Neurotoxicity

The test used was that known as the rota rod test described by BOISSIER (Therapie 1958 XIII pp. 1074–1118).

This test aims at determining the ability of mice to coordinate their movements by seeing to what extent they can remain on a roller turning at a rate of 4 revolutions per minute for two minutes. The trial was carried out thirty minutes after administration by oral route of the compound to be studied and the percentage of failures was noted.

The results obtained with compounds of the invention are listed hereunder:

| Compound | Dose administered (mg/kg) | % of failures |
|---|---|---|
| A | 175 | 0 |
|   | 600 | 30 |
| C | 370 | 50 |
| D | 250 | 50 |
| J | 500 | 0 |
| K | 600 | 0 |
| M | 635 | 0 |
| N | 720 | 0 |
| P | 690 | 0 |

The value of this test is twofold. Failure on the part of the animals gives a very early indication of the slightest damage to the meuromuscular functions which cannot be discerned by any other means. Secondly, this test serves as an element of comparison for drawing up index figures involving the results obtained with other tests.

Additional behaviour tests were undertaken with Compound A.

This compound showed, for example, a non-significant decrease of 12% in spontaneous motoricity in the mouse for 60 minutes after an oral dose of 175 mg/kg.

This test is described in U.S. Pat. No. 3,929,869.

In the traction test (Psychotropic Drugs, 1957, 373—391) which enables sense of balance as well as muscular tonus and strength to be determined the $ED_{50}$, i.e. the dose which causes 50% failures in the test, was found to be, in the case of Compound A, 60 minutes after administration, 600 mg/kg by oral route for mice.

Finally, the hypnotic action of Compound A was studied in mice by means of the test of the posture reflex, the animals being kept under observation during the four hours following the oral administration of the product.

In the test, no loss of the posture reflex was registered even at the maximum dose studied i.e. 1000 mg/kg.

II. Determination of tranquillizing properties

A. Anxiolytic action

The anxiolytic action was demonstrated by means of the "electrically-provoked combat" test (J. Pharmacol. Exp. Therap. 1959, 125–128) and the four plates test (European J. Pharmacol. 1968, 4, 141–151).

(a) "Electrically-provoked combat" test

Under certain conditions, a pair of mice reacts to an electric stimulus by a series of combats which are provoked by the animals as a result of the electric shock. This anxiety is expressed by a combat with the other animal which is rendered responsible. For this reason, the test described hereunder can be considered as a means of evaluating the anxiolytic action of a compound. Two mice which have been previously on a diet consisting only of water are placed together in a cage. They are then submitted to a series of electric impulses of an intensity varying between 40 and 80 volts according to the sensitivity of the animals. The test is first carried out with untreated animals as controls and then with the same animals treated 30 minutes before the test with a dose of the compound to be studied.

Note is taken on the number of combats engaged. The results are expressed in percentage of decrease in the number of combats engaged by the treated animals in comparison with the number of combats registered before treatment.

The following results were obtained:

| Compound | Dose administered (mg/kg) | % of decrease |
|---|---|---|
| A | 58 | 50 |
| B | 56.5 | 52 |
| C | 71 | 50 |
| D | 74 | 50 |
| E | 50 | 70 |
| F | 82 | 50 |
| G | 94 | 48 |
| H | 110 | 50 |
| I | 200 | 55 |
| J | 200 | 67 |
| K | 200 | 42 |
| L | 228 | 53 |
| M | 254 | 56 |
| N | 360 | 30 |
| P | 460 | 31 |

In a comparison carried out, under the same experimental conditions, diazepam and meprobamate were found to give, at the respective doses of 0.69 mg/kg and 70 mg/kg, 50% protection against anxiety.

A further comparison test carried out with Compound A, diazepam and meprobamate, showed that, at the dose at which each of these compounds provokes a 60%-decrease in the number of combats, no failure in the rota rod test was registered with Compound A while 12% and 35% of failures were observed with diazepam and meprobamate respectively.

Similarly, a decrease of 80% in the number of combats can be obtained with Compound A without any action on spontaneous motoricity, whereas with diazepam it is not possible to exceed a 15%-reduction in the number of combats without altering spontaneous motoricity. Thus, for example, with the dose of diazepam which produces a reduction of 80% in the number of combats, a 40%-decrease in spontaneous motoricity was registered.

(b) Four plates test

This test, which is specific to the anxiolytics, was undertaken with the mouse, thirty minutes after the oral administration of the compound to be studied.

It consists in placing mice in a box with fairly high walls, of which the bottom comprises four square plates. These plates, which all have the same dimensions, are separated from each other by a central axis and are alternately electrified by the positive and negative poles of a source of electric current. There is a space of a few millimeters between adjacent plates.

The mouse placed in this apparatus explores it and thus passes over the different plates in succession. Note is taken of the number of times each animal passes over the plates during one minute. When the current is switched on, the mouse passing over the plates receives an electric shock (80 V), which provokes a gradual decrease in the exploratory movements, and finally brings the animals to a complete stop.

Anxiolytic agents enable the animals to become more or less indifferent to the electric shock. As a consequence, the number of times the treated mouse passes over the plates, in spite of the shock, tends to come near to the number registered with the control animals which do not receive any shock.

The percentage of protection against anxiety given by compounds of the invention was calculated by comparing the number of times the control animals passed over the plates when electrified with the number of times the treated animals passed over the electrified plates.

The following results were registered:

| Compound | Dose administered (mg/kg) | % of protection |
|---|---|---|
| A | 175 | 25 |
| C | 105 | 50 |
| E | 100 | 27 |
| F | 175 | 16 |
| G | 282 | 18 |
| H | 250 | 39 |
| I | 150 | 29 |
| K | 300 | 25 |

For comparison purposes, the rota rod test and the test on spontaneous motoricity were carried out with diazepam and meprobamate using the particular dose of each of these compounds which offers a 25%-protection against anxiety in the four plates test. In this comparison, the $ED_{25}$ had to be used since it is not possible to obtain a $ED_{50}$ with diazepam in the four plates test because the sedative effects of this compound become too intense when a dose of more than 2 mg/kg is given. The results obtained are listed hereunder in comparison with those registered with Compound A:

| Compound | Rota rod (% of failures) | Spontaneous motoricity (% of decrease) |
|---|---|---|
| A 175 mg/kg | 0 | 12 |
| Diazepam 2 mg/kg | 35 | 57 |

-continued

| Compound | Rota rod (% of failures) | Spontaneous motoricity (% of decrease) |
|---|---|---|
| Meprobamate 79 mg/kg | 30 | 11 |

These results show that Compound A is the least sedative particularly when the percentage of failures in the rota rod test are compared. These figures prove that, with Compound A, a positive result can be obtained in the four plates test without any sedative effect, which is impossible with meprobamate and diazepam. Compound K has also been found be much less sedative than diazepam and meprobamate. An oral dose of 300 mg/kg in the mouse, which represents the $ED_{25}$ in the four plates test, was, in fact, found to provoke no failures in the rota rod test.

B. Antiaggressive activity

Aggressivity of the isolated mouse.

If a male mouse is isolated in a cage for three to four weeks, it will spontaneously attack any other animal of the same species which is placed in the same cage.

Mice wer isolated for the period of time required to render them spontaneously aggressive. Two mice, one rendered aggressive and one in a normal non-aggressive state, were then placed together and note was taken of the number of attacks by the aggressive mouse which occurred over a period of three minutes.

Each batch was composed of five pairs of animals.

The aggressive animals of each batch were then treated by oral route with the compound to be studied which was administered in such a way that the aggressive animals of each batch received a higher dose than those of the preceding batch.

Thirty minutes after administration, the couples were placed together again for a further three minutes and the number of attacks noted.

The $ED_{50}$ was then calculated i.e. the dose of the compound under study at which the number of attacks on the part of the treated animals was 50% less than the number of attacks made by the same animals before treatment.

In the case of Compound A, the $ED_{50}$ was 142 mg/kg.

Using the same experimental conditions, no results were obtained with diazepam up to 4 mg/kg. At a dose of 8 mg/kg, which is strongly sedative, a 38%-reduction in the number of attacks was obtained. In the case of meprobamate, the $ED_{50}$ was 170 mg/kg.

The aggressivity induced by isolating a mouse is a very accurate pharmacological test.

In the four plates test and in the "electrically-provoked combat" test, anxiety and aggressivity are conditions reactions while aggressivity in the isolated mouse is an acquired characteristic. In the first two cases, it may be supposed that the drugs may act either specifically on the particular type of behaviour or unspecifically by modifying the effects of the conditioning factor.

In the last case, it may be supposed that the drugs act only on behaviour either specifically or through a sedative action.

In the isolated mouse test, diazepam was found to be devoid of activity at least in the scale of doses utilized to obtain a positive effect in the four plates test and in the "electrically-provoked combat" test.

With regard to meprobamate, a dose of 170 mg/kg of this compound was found to be necessary to obtain a positive result in the isolated mouse test. At this dose, the sedative effects are considerable since it has been found to produce 75% in the rota rod test.

As against this, Compound A exerts an antiaggressive action starting from a dose of 100 mg/kg by oral route, which dose is entirely devoid of any sedative effects.

Compound A, therefore, exerts a specific action on aggressivity through an effect on behaviour and not through any sedative activity. In this respect, Compound A is markedly superior to the reference products since it will not induce either somnolence or sedation at doses which are active against aggressivity.

III Determination of anticonvulsant activity

Action on the pentylenetetrazole-induced seizure

The purpose of this test which is carried out on mice is to determine whether the compounds of the invention, when given preventively by oral route, are capable at certain doses of protecting some of the animals against the epileptic seizure produced by a predetermined dose of pentylenetetrazole which would be 100% fatal in the absence of the compound.

The compound to be studied was administered fifteen minutes before an injection of 125 mg/kg of pentylenetetrazole and note was taken of the number of deaths occurring during the three hours following this injection. The results were expressed in percentage of protection of the animals against death at the dose studied.

The following results were registered:

| Compound | Dose administered (mg/kg) | % of protection |
|---|---|---|
| A | 320 | 50 |
| C | 70 | 50 |
| D | 80.5 | 50 |
| E | 300 | 90 |
| F | 150 | 50 |
| G | 188 | 20 |
| K | 200 | 30 |
| N | 240 | 20 |

These results show that the compounds of the invention possess, as a general rule, weak anticonvulsant properties with the exception of Compounds C and D, the activity of which is this respect is considerable.

IV Determination of cholinolytic properties

Action with respect to tremorine

This test has been described by EVERETT (Nature, 1956, 177–238)

When injected into mice, tremorine produces peripheral cholinergic effects i.e. weeping, hypersalivation, sedation, diarrhea as well as central cholinergic effects i.e. tremors, akinesia.

Batches of 10 mice separated into individual cages, were given the compound to be studied, by oral route, 30 minutes before administration of an intraperitoneal dose of 100 mg/kg of tremorine.

Note was then taken in each batch of the percentage of animals presenting the various symptoms of tremorine-induced poisoning since at such a dose of tremorine 100% of the control animals are poisoned.

The results hereunder are expressed in percentage of mice protected against tremor at the dose of the compound of the invention which was administered:

| Compound | Dose administered (mg/kg) | % of protection |
|---|---|---|
| A | 200 | 0 |
| C | 170 | 0 |
| E | 100 | 0 |

Furthermore, at doses of 100, 300, 400 and 500 mg/kg, by oral route, Compound A did not protect any animal against the central or peripheral cholinergic effects provoked by tremorine.

Therefore, the compounds of the invention are devoid of any anticholinergic action in the above test.

V Determination of acute toxicity

Acute toxicity was determined on Swiss E.O.P.S. mice, by oral route, using the technique of LITCHFIELD and WILCOXON (J. Pharmacol. Exp. Ther. 1946, 96, 99).

In the case of Compound A, the $LD_{50}$ was far above 3000 mg/kg both in mice and rats.

At a dose of 3000 mg/kg, in fact, only 5% of deaths were observed in mice and 10% in rats during the 8-day period of observation.

Regarding the other compounds of the invention, the $LD_0$ in mice, i.e. the highest dose at which no death occurs during the period of observation, is as a general rule, superior to 600 mg/kg when administered by oral route.

It will be appreciated that for therapeutic use the compounds of the invention will normally be administered in the form of a pharmaceutical or veterinary composition in a dosage unit form appropriate to the required mode of administration, the composition comprising as active ingredient at least one compound of the invention in association with a pharmaceutical carrier or excipient therfor.

For oral administration, the composition may take the form of, for example, a coated or uncoated tablet, a hard- or soft-gelatin capsule, a suspension or a syrup. The composition may alternatively take the form of a suppository for rectal administration.

When in dosage unit form, the composition may contain from 50 to 500 mg, preferably 200 to 250 mg, of the active principle per dosage unit for oral administration and rectal administration.

The compositions of the invention will be prepared by associating at least one of the compounds of formula I with at least one appropriate carrier or excipient therefor.

Examples of suitable carriers or excipients are distilled water, talc, magnesium stearate, colloidal silica, milk sugar, saccharose, carboxymethylcellulose, wheat and corn starches, kaolin, levilite, cocoa butter.

The following Examples illustrate the preparation of the compounds of formula I as well as of a therapeutic composition:

EXAMPLE 1

Preparation of 1-(1,1-di-n-propyl-n-butyl)-urea or tri-n-propylmethylurea

In a 3-necked flask, equipped with a condenser, a thermometer and a dip-tube, gaseous ammonia was bubbled through 300 ml of dry dioxan. Into the ammonia-saturated solution, maintained at a temperature of 60° C., 17 g (0.092 mol) of freshly redistilled 1,1-di-n-propyl-n-butylisocyanate were introduced over a period of 90 minutes. When the operation of addition was finished, the solution was heated under reflux for one hour and then the dioxan was evaporated off under reduced pressure. The colorless crystals so obtained were then recrystallized from 60 ml of acetonitrile.

In this manner, 14 g of 1-(1,1-di-n-propyl-n-butyl)-urea were obtained in the form of colorless crystals.

M.P.: 123° C.

Yield: 76%

In accordance with a variation of the above procedure, a concentrated ammonia solution (d = 0.92) was used in place of an ammonia solution in dioxan.

Following the same procedure as that described above but using the appropriate starting-products, the compounds hereunder were prepared.

| Compound | M.P. in °C. |
|---|---|
| 1-(1,1-Diethyl-n-propyl)-urea (Yield : 84%) | 157.6 |
| 1-(1-Methyl-1-ethyl-n-pentyl)-urea (Yield : 60%) | 84.5 |
| 1-(1-n-Propyl-1-isopropyl-n-butyl)-urea (Yield : 70%) | 129.8 |
| 1-(1,1-Di-n-propyl-3-methyl-n-butyl)-urea (Yield : 77%) | 129.6 |
| 1-(1,1-Di-n-butyl-n-pentyl)-urea (Yield : 65%) | 154.4 |
| 1-(1,1-Di-n-propyl-3-butenyl)-urea (Yield : 68%) | 104.2 |

The compounds listed above were purified by recrystallization from acetonitrile with the exception of 1-(1,1-diethyl-n-propyl)-urea which was recrystallized from a 80/20 mixture of acetonitrile/water.

EXAMPLE 2

Preparation of 1-(1,1-diethyl-2-propynyl)-urea

While stirring, 11.1 g (0.1 mol) of 1-(1,1-diethyl-2-propynyl)-amine, 10.5 g of nitrourea and 40 ml of distilled water were heated for three hours at 50° C. The insoluble product so obtained was filtered out, washed with water and then dried.

In this manner, 6.6 g of (1-(1,1-diethyl-2-propynyl)-urea were obtained, in the form of colourless crystals, after recrystallization from ethyl acetate.

M.P.: 108° C.

Yield: 40%

Following the same procedure as that described above but using the appropriate starting-products, the compounds hereunder were prepared:

| Compound | M.P. in °C. |
|---|---|
| 1-(1,1-Di-n-propyl-2-pentynyl)-urea | 126 |
| 1-(1,1-Di-n-propyl-2-butynyl)-urea | 98.8 |

The above compounds were recrystallized from ethyl acetate.

EXAMPLE 3

Preparation of 1(1,1-di-n-propyl-n-butyl)-3-(2-propenyl)-urea

To a solution of 3.66 g (0.02 mol) of 1,1-di-n-propyl-n-butylisocyanate dissolved in 20 ml of heptane, 1.14 g (0.02 mol) of allylamine were added. The mixture was stirred and heated at 60° C. for 2 hours. The heptane was then evaporated off under vacuum and the product so obtained was recrystallized from acetonitrile containing 30% water.

In this manner, 3.6 g of 1-(1,1-di-n-propyl-n-butyl)-3-(2-propenyl)-urea were obtained in the form of colourless crystals.

M.P.: 66° C.
Yield: 75%

Following the same procedure as that described above but using the appropriate starting-products, the compounds listed hereunder were prepared:

| Compound | M.P. in °C. |
|---|---|
| 1-(1,1-Di-n-propyl-3-butenyl)-3-methyl-urea (Yield : 40%) | 111.3 |
| 1-(1,1-Di-n-propyl-n-butyl)-3-(2-propynyl)-urea (Yield : 54%) | 82.3 |

EXAMPLE 4

Preparation 1-(1,1-di-n-propyl-n-butyl)-3-methyl-urea

To a solution of 7.9 g (0.05 mol) of 1,1-di-n-propyl-n-butylamine in ether, 3.42 g (0.06 mol) of methyl isocyanate dissolved in 15 ml of ether were slowly added. The mixture was stirred for 10 minutes at room-temperature and then concentrated to dryness.

In this manner, 7.1 g of 1-(1,1-di-n-propyl-n-butyl)-3-methyl-urea were obtained in the form of colourless crystals, after recrystallization from isopropyl ether.

M.P.: 120° C.
Yield: 67%

EXAMPLE 5

Preparation of 1-(1,1-di-n-propyl-n-butyl)-3,3-dimethyl-urea

To 3.66 g (0.02 mol) of 1,1-di-n-propyl-n-butylisocyanate maintained under stirring, 2.5 ml of a 40%-aqueous solution of dimethylamine were progressively added. A colourless product precipitated. After the operation of adding the amine was finished, 10 ml of distilled water were introduced and the stirring of the mixture was continued for 2 hours. The crystals so obtained were filtered out and recrystallized from heptane containing 20% cyclohexane.

In this manner, 3.6 g of 1-(1,1-di-n-propyl-n-butyl)-3,3-dimethyl-urea were obtained in the form of colourless crystals.

M.P.: 88° C.
Yield: 80%

EXAMPLE 6

In accordance with known pharmaceutical techniques, hard-gelatin capsules were prepared containing the following ingredients:

| Ingredient | mg per capsule |
|---|---|
| 1-(1,1-Di-n-propyl-n-butyl)-urea | 200 |
| Corn starch | 139 |
| Colloidal silica | 1 |
|  | 340 |

We claim:

1. A method of treating pathological states of anxiety and aggressivity in a host in need of such treatment, comprising the administration to said host of an effective dose of at least one urea derivative of the general formula:

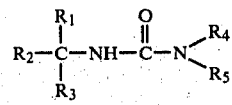

wherein $R_1$, $R_2$ and $R_3$, which are the same or different, each represent a straight- or branched-chain alkyl, alkenyl or alkynyl radical having from 1 to 5 carbon atoms, $R_4$ and $R_5$ which are the same or different, each represent a hydrogen atom or a straight- or branched-chain alkyl, alkenyl or alkynyl radical having from 1 to 5 carbon atoms, $R_1$, $R_2$ and $R_3$ being such that:

(a) only one of these radicals can represent an alkenyl or alkynyl group having an unsaturated bond in the $\alpha$, $\beta$-position with respect to the methylurea radical, in this case, each of the other two substituents represents an alkyl radical, (b) the sum of their carbon atoms is never inferior to 4.

2. A method of treating pathological states of anxiety and aggressivity in a host in need of such treatment, comprising the administration to said host of an effective dose of 1-(1,1-di-n-propyl-n-butyl)-urea.

3. A method according to claim 1 or 2 whereby the effective daily dosage of the urea derivative for a human host weighting 60 kilos is between 400 and 1200 mg.

* * * * *